(12) United States Patent
López Nieto et al.

(10) Patent No.: US 7,319,179 B2
(45) Date of Patent: Jan. 15, 2008

(54) METHOD FOR THE OXIDATIVE DEHYDROGENATION OF ETHANE

(75) Inventors: José Manuel López Nieto, Valencia (ES); Pablo Botella Asunción, Valencia (ES); Maria Isabel Vazquez Navarro, Valencia (ES); Ana Dejoz García, Valencia (ES)

(73) Assignees: Consejo Superior de Investigaciones Cientificas, Madrid (ES); Universidad Politecnica de Valencia, Valencia (ES)

( * ) Notice: Subject to any disclaimer, the term of this patent is extended or adjusted under 35 U.S.C. 154(b) by 217 days.

(21) Appl. No.: 10/909,276

(22) Filed: Jul. 30, 2004

(65) Prior Publication Data

US 2005/0085678 A1 Apr. 21, 2005

Related U.S. Application Data

(63) Continuation of application No. PCT/ES03/00056, filed on Jan. 31, 2003.

(30) Foreign Application Priority Data

Jan. 31, 2002 (ES) .............................. 200200276

(51) Int. Cl.
*C07C 5/327* (2006.01)
*C07C 5/333* (2006.01)
*B01J 23/00* (2006.01)

(52) U.S. Cl. ...................... 585/658; 585/661; 585/662; 585/663; 502/302; 502/306; 502/308; 502/309; 502/310; 502/311; 502/312; 502/315; 502/316; 502/317; 502/318; 502/319; 502/321; 502/328; 502/330; 502/331; 502/337; 502/338; 502/345; 502/350; 502/352; 502/353

(58) Field of Classification Search ................ 585/658, 585/661–663
See application file for complete search history.

(56) References Cited

U.S. PATENT DOCUMENTS

| 4,250,346 A | 2/1981 | Young et al. |
| 4,524,236 A | 6/1985 | McCain |
| 5,281,745 A * | 1/1994 | Ushikubo et al. ........... 558/319 |
| 6,013,597 A | 1/2000 | Karim et al. |

FOREIGN PATENT DOCUMENTS

EP 0 294 845 A1 12/1988

(Continued)

OTHER PUBLICATIONS

Lopez Nieto, JM, et al., The selective oxidative dehydrogenation of ethane over hydrothermally synthesised MoVTeNb catalysts, Chem. Comm., 2002, vol. 17, pp. 1906-1907.

(Continued)

*Primary Examiner*—Glenn Caldarola
*Assistant Examiner*—In Suk Bullock
(74) *Attorney, Agent, or Firm*—Klauber & Jackson L.L.C.

(57) ABSTRACT

The invention relates to a method for the oxidative dehydrogenation of ethane. The inventive method is characterized in that it consists of bringing the ethane into contact with the catalyst containing Mo, Te, V, Nb and at least a fifth element A which is selected from Cu, Ta, Sn, Se, W, Ti, Fe, Co, Ni, Cr, Zr, Sb, Bi, an alkali metal, an alkaline-earth metal and a rare earth, in which at least Mo, Te, V and Nb are present in the form of at least one oxide, said catalyst presenting, in calcined form, an X-ray diffractogram with more than ten intense diffraction lines, typically, the most intense lines corresponding to diffraction angles 2Θ of 7.7°±0.4, 8.9°±0.4, 22.1°+0.4, 26.6°±0.4, 26.9°±0.4, 27.1°±0.4, 28.1°±0.4, 31.2°±0.4, 35.0°±0.4 and 45.06°±0.

24 Claims, 7 Drawing Sheets

FOREIGN PATENT DOCUMENTS

| | | |
|---|---|---|
| EP | 0294845 B1 | 6/1992 |
| JP | 07053414 | 2/1995 |
| JP | 10017523 | 1/1998 |
| JP | 10175885 | 6/1998 |
| JP | 11043314 | 2/1999 |
| WO | 98/02791 | 9/1998 |
| WO | WO 99/13980 * | 3/1999 |
| WO | 02/00357 | 6/2002 |
| WO | WO 03/008096 A1 | 1/2003 |

OTHER PUBLICATIONS

Wataru Ueda et al, Selective oxidation of light alkanes over hydrothermally synthesized Mo-V-M-O (M=Al, Ga, Bi, Sb, and Te) oxide catalysts, Applied Catalysis A: General 200 (2000) 135-143.

Thorsteinson et al, The oxidative Dehydrogenation of Ethane over Catalysts Containing Mixed Oxides of Molybdenum and Vanadium, Journal of Catalysts 52, 116-132 (1978).

* cited by examiner

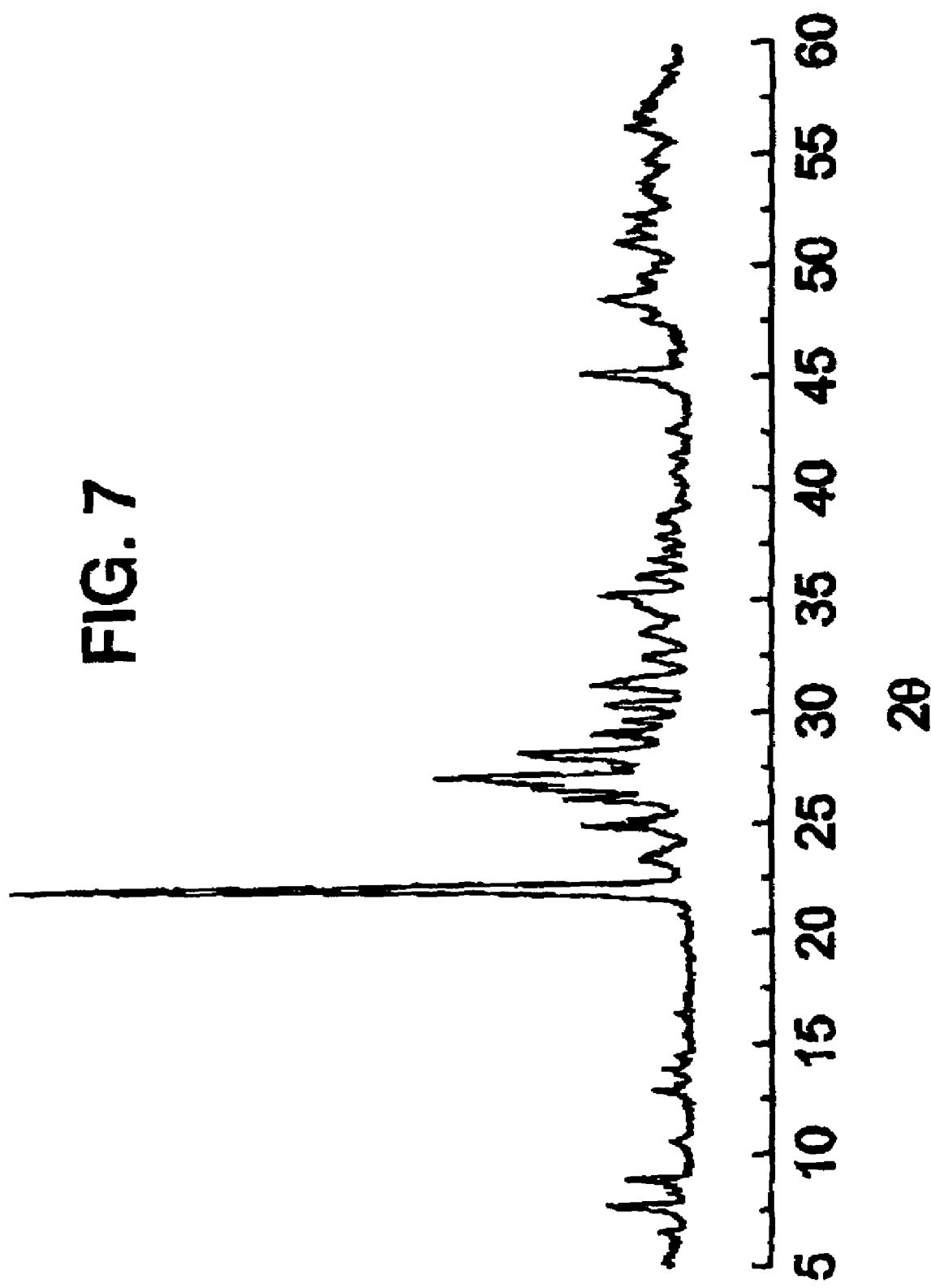

METHOD FOR THE OXIDATIVE DEHYDROGENATION OF ETHANE

This application is a continuation division of international application number PCT ES03/00056, filed Jan. 31, 2003.

FIELD OF THE ART

The present invention comes within the technical field of petrochemical processes. In particular, it refers to an oxidation process of ethane and more specifically to the oxidative dehydrogenation of ethane for the obtaining of ethene.

STATE OF THE ART PRIOR TO THE INVENTION

Ethene is currently obtained starting from the catalytic cracking of petroleum or by catalytic dehydrogenation of ethane. For economic and technical reasons, it is of industrial interest to obtain olefins starting from saturated hydrocarbons by oxidative dehydrogenation reactions (in the presence of oxygen or air). Nevertheless, so far, there do not exist any catalysts displaying high effectivity.

Catalysts based on metallic oxides MoVZ (Z=Li, Na, Be, Mg, Ca, Sr, Ba, Ca, Sr, Zn, Cd, Hg, Sc, Y, La, Ce, Al, Ti, Ti, Zr, Hf, Pb, Bn, Ta, As, Sb, Bi, Cr, W, U, Te, Fe, Co and Ni) for the oxidative dehydrogenation of ethane to ethene are described in European patent EP-294,845 (1988).

Catalysts based on metallic oxides $MO_aX_bY_c$ in which X can be one or more elements (Cr, Mn, Ta, Ti, V and W) and Y is Bi, Ce, Co, Cu, Fe, K, Mg, Ni, P, Pb, Sb, Si, Sn, Tl or U for the oxidative dehydrogenation of ethane to ethene are described in U.S. patent U.S. Pat. No. 4,250,346, nevertheless, the reference solely proposes the obtaining of ethene with high selectivity.

The use of catalysts based on oxides of MoVNb had already been proposed by Thorsteinson et al. in "The oxidative dehydrogenation of Ethane over catalyst containing Mixed Oxides of Molybdenum and Vanadium", *J. Catal.* 52, 116-132 (1978).

Metallic oxides of Mo—V—Nb—Sb are more effective for the selective oxidation of ethane to ethene as revealed by, for example, U.S. Pat. No. 4,524,236 (1985); JP-10175885 (1988).

In patent U.S. Pat. No. 4,524,236, the MoVNbSbM system is presented (M=Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, W or Mn). In this patent it is described that in the oxidation of ethane on a catalyst $Mo_{0.61}V_{0.16}Nb_{0.07}Sb_{0.04}$ an ethane conversion of 34% is obtained at 320° C. with a selectivity to ethene of 86%.

In the patent JP-10143314, the system MoVSbX is described (X=Ti, Zr, Nb, Ta, Cr, W, Mn, Fe, Ru, Co, Rh, Ir, Ni, Pd, Pt, Cu, Ag, Zn, In, Sn, Pb, Bi, Ce and alkaline earth metals) with a crystalline structure defined by a diffractogram that is illustrated in the patent.

In the Japanese patent JP-07053414 (patent written in Japanese) an active and selective catalyst is proposed for the oxidative dehydrogenation of ethane to ethene based on oxides of MoVTeNb ($Mo_1V_{0.3}Te_{0.23}Nb_{0.12}$), having an X-ray diffractogram at 2Θ=22.1; 28.2; 36.2; 45.1, 50.0.

Metallic oxides of Mo—V—Nb—Sb have also been proposed as an effective system for the oxidation of ethane and ethene to acetic acid in EP-A-0294845.

In patent WO-99/13980 a catalyst is described with Mo, V and Nb and small quantities of phosphorus, boron, hafnium, tellurium and/or arsenic with calcination temperatures (in air) between 250-450° C. for the oxidation of ethane to acetic acid with yields of 12.3-26.6%.

In Japanese patent JP-10017523 (1998) a catalyst is proposed consisting of a metal (Ru, Rh, Ir, Pd and/or Pt) supported on an oxide of Mo—V—X-Z. In that patent it is described that a catalyst of Pd supported on an oxide of Mo—V—Nb—Sb gives rise to a yield of acetic acid of 59.7% in the oxidation of ethene at 320° C.

Ueda et al. (Applied Catalysis, 200 (2000) 135) observe that catalysts of the type Mo—V-M-O (M=Al, Ga, Bi, Sb and Te), hydrothermally prepared, are active and selective in the oxidation of ethane to ethene with selectivities to ethene lower than 75% for ethane conversions lower than 20%.

Finally, the Spanish patent application P200101756 describes catalysts containing Mo—Te—V—Cu and at least another component A selected from among Nb, Ta, Sn, Se, W, Ti, Fe, Co, Ni, Cr, Ga, Sb, Bi, a rare earth, alkaline or alkaline earth, for the oxidation of alkanes; but it has not been proven that said catalysts give rise to an oxidation of ethane with the necessary yield desired at the industrial scale.

DESCRIPTION OF THE INVENTION

The present invention refers to a method for the oxidative dehydrogenation of ethane, characterized in that it consists of placing ethane in contact with a catalyst containing Mo, Te, V, Nb and at least a fifth element A which is selected from Cu, Ta, Sn, Se, W, Ti, Fe, Co, Ni, Cr, Zr, Sb, Bi, an alkali metal, an alkaline-earth metal and a rare earth, in which at least Mo, Te, V and Nb are present in the form of at least one oxide, said catalyst presenting, in calcined form, an X-ray diffractogram with more than ten intense diffraction lines, typically, the most intense lines corresponding to diffraction angles 2Θ of 7.7°±0.4, 8.9°±0.4, 22.1°±0.4, 26.6°±0.4, 26.9°±0.4, 27.1°±0.4, 28.1°±0.4, 31.2°±0.4, 35.0°±0.4 and 45.06°±0.4.

In a preferred embodiment of the method, in the catalyst at least Mo, Te, V and Nb are present in the form of at least one calcined mixed oxide.

In a preferred embodiment, the catalyst has the empirical formula $$MoTe_hV_iNb_jA_kO_x$$

in which h, i and j have values lying between 0.001 and 4.0, k lies between 0.0001 and 2.0 and x depends on the oxidation state or valence of the elements Mo, Te, V, Nb and A, in other words, the quantity "x" of oxygen in the catalyst depends on the composition and method of activation.

In a preferred embodiment the above parameters present the following values and ratios:

h and i are comprised between 0.01 and 3, preferably between 0.02 and 2, the ratio i/h is comprised between 0.3 and 10, j is comprised between 0.001 and 2, preferably between 0.001 and 0.5, and k is comprised between 0.0001 and 2.0, preferably between 0.001 and 1.0.

In an additional preferred embodiment, A is Cu, W or Bi. In a yet more preferred embodiment, A is Cu, W or Bi and the above parameters take the following values:

h and i are comprised between 0.02 and 2, the ratio i/h is comprised between 0.3 and 10, j is comprised between 0.001 and 1.5, and k is comprised between 0.001 and 2.0.

According to the method of the invention, the catalyst can be a mixed oxide supported on a solid, such as for example silica, alumina, titanium oxide and mixtures thereof. In a preferred manner, the silica as solid support is present in proportion of 20 to 70% by weight with respect to the total weight of catalyst. Moreover, the catalyst can also be in the form of a mixed oxide supported on a silicon carbide.

Typically, in its calcined form, the catalyst presents an X-ray diffractogram whose most intense diffraction lines, along with the corresponding intensities relative to the peak of greatest intensity, are those shown in Table 1.

TABLE 1

| Diffraction angle 2Θ (±0.4°) | Mean spacing (Å) | Relative Intensity |
|---|---|---|
| 7.7 | 11.47 | 10-40 |
| 8.9 | 9.93 | 10-40 |
| 22.1 | 4.02 | 100 |
| 26.6 | 3.35 | 10-90 |
| 26.9 | 3.31 | 20-80 |
| 27.1 | 3.29 | 20-120 |
| 28.1 | 3.17 | 20-120 |
| 31.2 | 2.86 | 10-90 |
| 35.0 | 2.56 | 10-90 |
| 45.1 | 2.01 | 10-60 |

Said catalyst can be prepared by conventional methods starting from solutions of compounds of the different elements, from solutions of the pure elements themselves, or mixtures of both, with the desired atomic ratios. Said solutions are preferably aqueous solutions.

The method for preparation of the catalyst comprises at least:

a first stage, of mixing the compounds of the different elements, of pure elements or of a mixture of both.

a second stage, of drying the solid obtained in the first stage, and a third stage, of calcination of the dry solid obtained in the second stage.

The mixing stage can be done starting from the compounds of the different elements, starting from the actual pure elements in solution, or by hydrothermal methods.

The elements Mo, Te, V and Nb can be incorporated into the mixing stage as pure metallic elements, as salts, as oxides, as hydroxides, as alcoxides, as acids, or as mixtures of two or more of the above-mentioned forms. As salts, use is preferably made of sulphates, nitrates, oxalates or halides, and more preferably sulphates.

The Mo can be incorporated at the mixing stage, preferably as molybdic acid, ammonium molybdate, ammonium heptamolybdate and molybdenum oxide.

The Te can be incorporated at the mixing stage, preferably as telluric acid, ammonium tellurium oxide and metallic tellurium.

The V can be incorporated at the mixing stage, preferably as ammonium vanadate, vanadium oxide, vanadyl sulphate, vanadyl oxalate or vanadyl chloride.

The Nb can be incorporated at the mixing stage, preferably as niobium pentoxide, niobium oxalate, niobium chloride or Nb metal.

The elements Cu, W, Bi, Ta, Sn, Se, Ti, Fe, Co, Ni, Cr, Ga, Sb, Zr, rare earth, alkaline metal or alkaline earth metal can also be incorporated at the mixing stage as salts, oxides, hydroxides or alcoxides, pure or as mixtures of two or more elements. They are preferably incorporated as sulphates, nitrates, oxalates or halides, and more preferably as sulphates.

The mixing stage can be followed by a period of static permanence in the reactor, or the mixing can be carried out with stirring. Both the static permanence and the stirring can be done in a normal reactor or in an autoclave.

The mixing stage can be carried out in solution or by means of hydrothermal treatment.

The drying stage can be carried out by conventional methods in a kiln, evaporation with stirring, evaporation in a rotavapor or vacuum drying.

The calcination stage of the dry solid can be carried out in an inert gas atmosphere, such as for example nitrogen, helium, argon or mixtures, of air or mixtures.

An alternative embodiment of the method is, as stated earlier, carried out by employing hydrothermal methods (containing two or more elements in the synthesis, especially containing Mo, Te, V and Nb). The synthesis temperature and time can be determining conditions using hydrothermal methods. So, the synthesis temperature is preferably between 100 and 250° C. and, more specifically, between 150 and 180° C. The synthesis time is preferably between 6 and 500 hours, and more specifically between 24 and 200 hours.

The calcination stage can be carried out by causing a flow of inert gas to pass (with spatial velocities between 1 and 400 $h^{-1}$) or statically. The temperature lies between 250 and 1000° C. and more preferably between 550 and 800° C. The calcination time is not a determining factor, though between 0.5 hours and 20 hours is preferred. The speed of heating is not a determining factor, though between 0.1° C./minute and 10° C./minute is preferred. The catalyst can also be initially calcined in an oxidizing atmosphere up to a temperature of 200-350° C., and more preferably between 250 and 290° C., and later be subjected to a calcination in an inert atmosphere.

The elements Cu, W, Bu, Ta, Sn, Se, Ti, Fe, Co, Ni, Cr, Ga, Sb, Zr, rare earth, alkaline metal or alkaline earth metal can also be incorporated after the calcination stage by impregnation or precipitation. In this case, the resulting solid will be subjected to a second calcination stage.

The catalyst for the method of the present invention can be used as it is obtained once calcined.

In an alternative embodiment the catalyst can be supported on a solid such as: silica, alumina, titanium oxide or mixtures thereof, as well as silicon carbide. In these cases, the fixing of the different elements of the catalyst on the support can be done by conventional methods of impregnation, such as pore volume, excess solution, or simply by precipitation on the support of a solution containing the active elements.

The method of oxidative dehydrogenation of ethane according to the present invention converts ethane to ethene in accordance with a preferred embodiment. The method which gives rise to ethene is preferably carried out in gaseous phase and in the presence of water vapour.

According to an alternative embodiment of the present invention, the oxidative dehydrogenation of the ethane to ethene gives rise to acetic acid by reaction of ethane and oxygen in gaseous phase, in the presence of water.

According to an additional alternative embodiment of the method of the present invention, the oxidative dehydrogenation of the ethane gives rise to acetonitrile by reaction of ethane and oxygen, in the gaseous phase, in the presence of ammonia and water vapour.

According to an additional alternative embodiment of the method of the present invention, the oxidative dehydrogenation of the ethane to ethene or to acetic acid is carried out using the catalyst described as co-catalyst.

According to an additional alternative embodiment of the method of the present invention, the oxidative dehydrogenation of the ethane to acetonitrile is carried out using the catalyst described as co-catalyst and producing the ammoxidation of ethane.

According-to an additional alternative embodiment of the method of the present invention, the oxidative dehydrogenation of the ethane produces ethylene oxide and said oxidative dehydrogenation of ethane is carried out using the catalyst as co-catalyst with oxidation of ethane to ethylene oxide taking place.

In accordance with the method of the present invention pure oxygen, air, oxygen-inert gas mixtures (with different proportions of both) or oxygen-enriched air can be used as oxidizing agent.

In the process of oxidative dehydrogenation and of oxidation, the water may or may not be incorporated into the supply. The water content in the reaction mixture can be from 0 to 80% and more preferably between 20 and 60%.

In the method of oxidative dehydrogenation of ethane to ethene an increase is observed in the selectivity of ethene when the reaction is carried out in the presence of water vapour.

The method for oxidative dehydrogenation can be carried out in a fixed bed reactor or in a fluidized bed reactor. The reaction temperature lies between 250 and 550° C., preferably between 300 and 480° C., and more preferably between 350 and 440° C. The contact time, defined as the ratio between the volume of catalyst (W) and the total flow of supply gases (F), lies between 0.001 and 100 s. Although the contact time depends on the preparation method and composition of the catalyst used, in general it preferably lies between 0.05 and 50, and more preferably between 0.1 and 25 s.

BRIEF DESCRIPTION OF THE FIGURES

FIG. 7 shows an-X-ray difractogram of the catalyst described in example 15.

EXAMPLES

The invention will now be illustrated on the basis of some examples.

Example 1

Preparation of an Oxidation Catalyst Based on a Mixed Oxide of Mo—Te—V—Nb—O by the Hydrothermal Method 26.5 g of ammonium heptamolybdate tetrahydrate and 5.75 g of telluric acid are dissolved in 195.0 g of water at 80° C. Ammonium hydroxide (25% aqueous solution) is then added as far as pH=7.5. The water is evaporated from the solution obtained, with stirring, at 80° C. The resulting solid is dried in a kiln at 90° C. with the solid MT being obtained.

Figure 1:
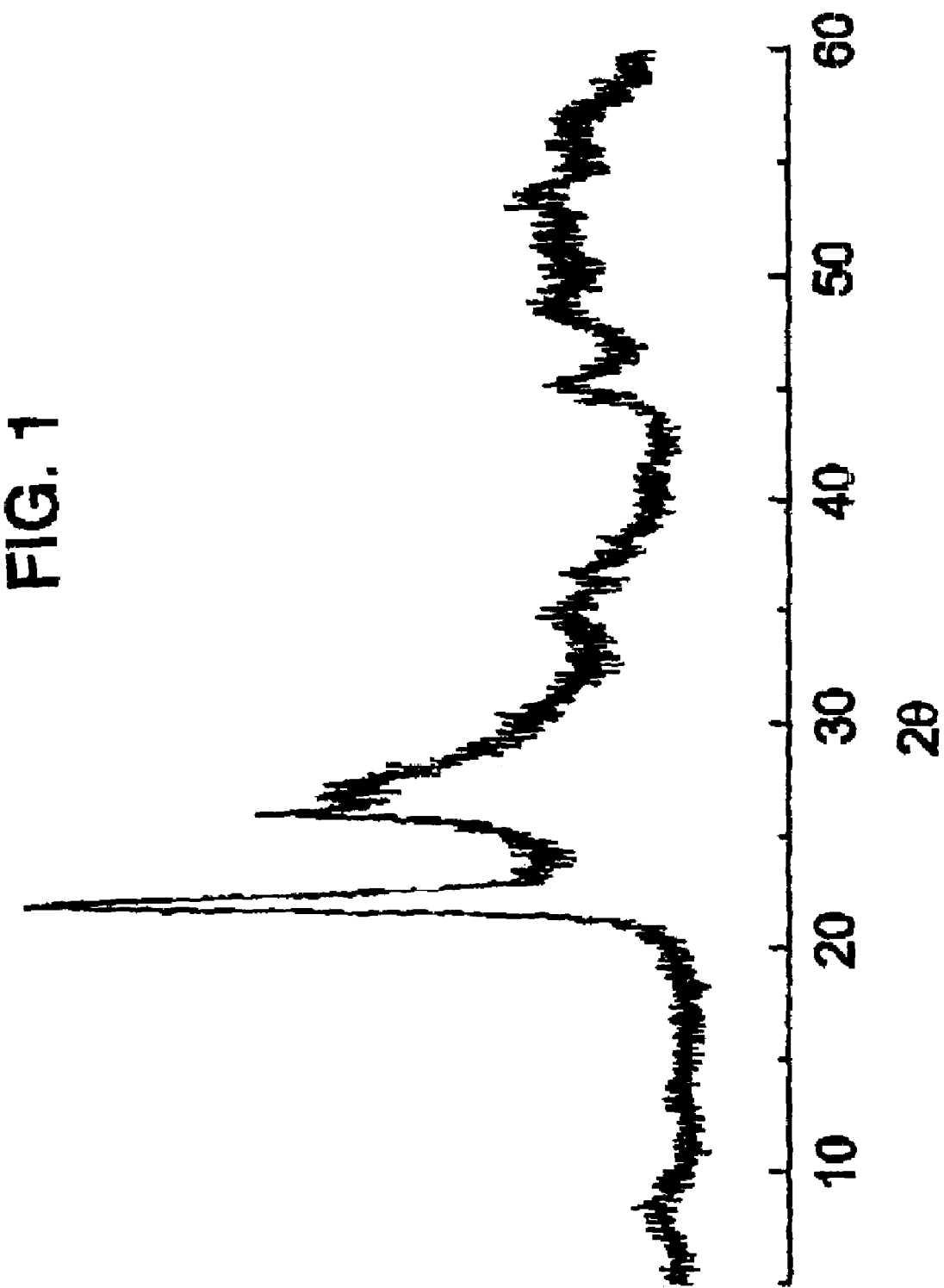
FIG. 1 shows an-X-ray difractogram of the catalyst described in example 1.

30.0 g of the solid MT are suspended in 213.30 g of water at 80° C. and 9.01 g of yanadyl sulphate and 10.39 g of niobium (V) oxalate are added. The mixture is stirred and transferred to a steel autoclave with an internal lining of teflon. The autoclave is kept at 175° C., static, for 2 days The content of the autoclave is filtered, it is washed with distilled water and dried at 80° C. The solid obtained is calcined at 450° C. for 2 h in a current of nitrogen in order to obtain the catalyst. This catalyst is characterized by presenting an X-ray difractogram as shown in FIG. 1.

Example 2

Use of the Catalyst Described in Example 1 for the Oxidative Dehydrogenation of Ethane 4.0 g of the catalyst described in example 1 were introduced into a fixed bed quartz reactor. The reaction was carried out using a mixture of gases, with a molar ratio of ethane:oxygen:helium=30/20/50, at a reaction temperature of 400° C. and a contact time, W/F, of 160 $g_{cat}$ h/(mol$_{C2}$). The results are shown in table 2.

Example 3

Figure 2:
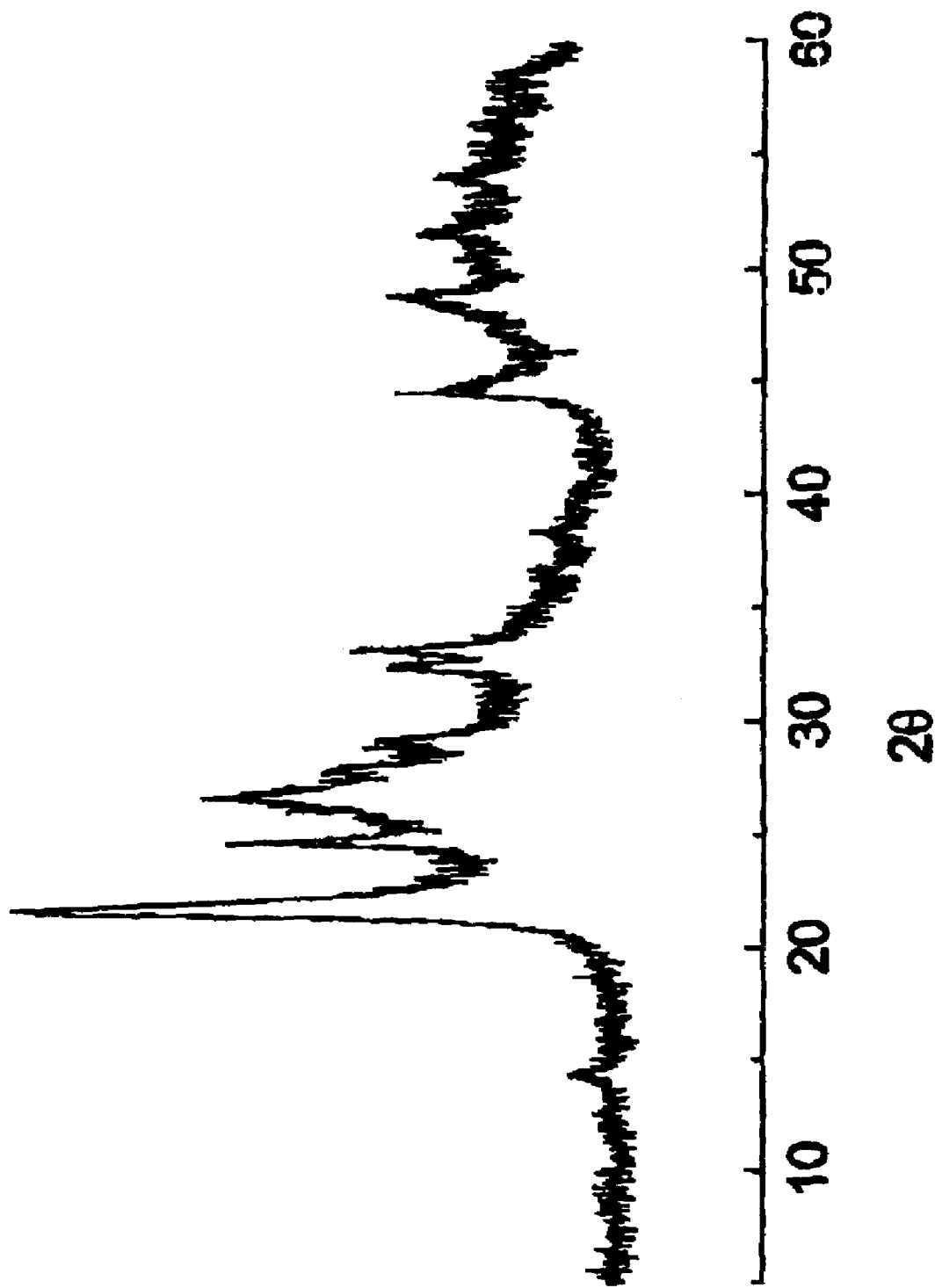
FIG. 2 shows an-X-ray difractogram of the catalyst described in example 3.

Preparation of an Oxidation Catalyst Based on a Mixed Oxide of Mo—V—Nb—O 80.0 g of ammonium heptamolybdate tetrahydrate and 15.87 g of ammonium metavanadate were dissolved in 1307 ml of hot water at 80° C. obtaining a uniform solution. Also, and after warming to 40° C., a solution (356.8 g) was prepared of niobium oxalate containing 53.97 millimols of niobium and it was added to the above solution obtaining a solution. The water of this solution was eliminated by evaporating with a rotavapor at 50° C., obtaining a solid. This solid was dried in a kiln at 110° C. for 24 h and was ground in order to obtain particle sizes of less than 0.25 mm. The resulting powder was calcined at 450° C. for 2 h in a nitrogen atmosphere in order to obtain the catalyst. The X-ray difractogram of that catalyst is shown in FIG. 2.

Example 4

Use of the Catalyst Described in Example 3 for the Oxidative Dehydrogenation of Ethane 1.0 g of the catalyst described in example 3 was introduced into a fixed bed quartz reactor. The reaction was carried out using a mixture of gases, with a molar ratio of ethane:oxygen:helium=30/10/60, at a reaction temperature of 400° C. and a contact time, W/F, of 20.4 $g_{cat}$ h/(mol$_{C2}$). The results are shown in table 2. From the result obtained it can be deduced that the presence of tellurium in the catalyst produces an increase in both the conversion of ethane and of the selectivity to ethene.

Example 5

Preparation of an Oxidation Catalyst Based on a Mixed Oxide of Mo—Te—V—O by the Hydrothermal Method 26.5 g of ammonium heptamolybdate tetrahydrate and 5.75 g of telluric acid are dissolved in 195.0 g of water at 80° C. Ammonium hydroxide (25% aqueous solution) is then added as far as pH=7.5. The water is evaporated from the solution obtained, with stirring, at 80° C. The resulting solid is dried in a kiln at 90° C. with the solid MT being obtained.

Figure 3:
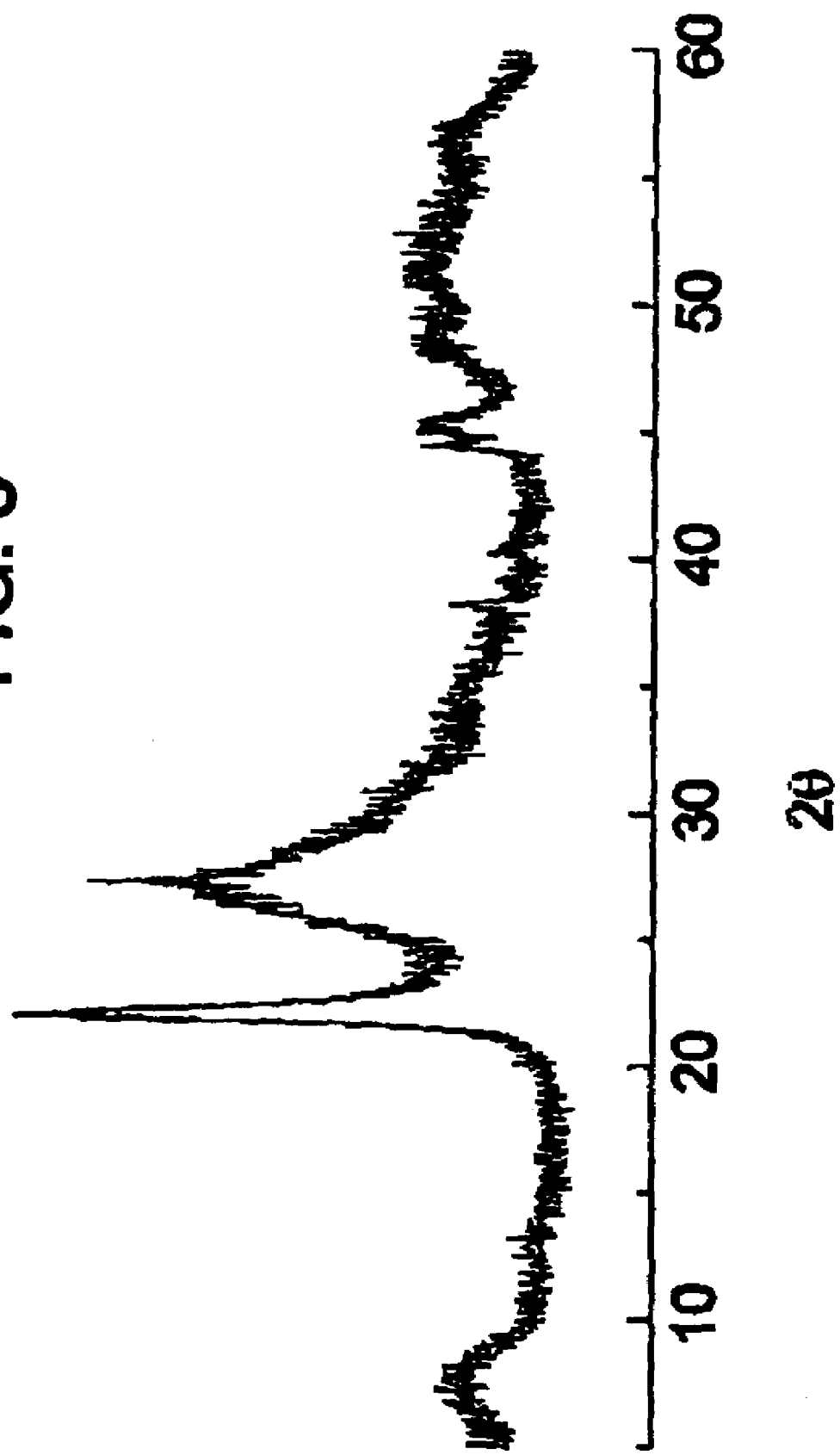
FIG. 3 shows an-X-ray difractogram of the catalyst described in example 5.

30.0 g of the solid MT are suspended in 213.30 g of water at 80° C. and 9.01 g of vanadyl sulphate are added. The mixture is stirred and transferred to a steel autoclave with an internal lining of teflon. The autoclave is kept at 175° C., static, for 2 days The content of the autoclave is filtered, it is washed with distilled water and dried at 80° C. The solid obtained is calcined at 450° C. for 2 h in a current of nitrogen in order to obtain the catalyst. This catalyst is characterized by presenting an X-ray diffractogram as shown in FIG. 3.

Example 6

Use of the Catalyst Described in Example 5 for the Oxidative Dehydrogenation of Ethane 4.0 g of the catalyst described in example 5 were introduced into a fixed bed quartz reactor. The reaction was carried out using a mixture of gases, with a molar ratio of ethane:oxygen:helium=30/10/60, at a reaction temperature of 400° C. and a contact time, W/F, of 240 $g_{cat}h/(mo_{C2})$. The results are shown in table 2.

Example 7

Preparation of an Oxidation Catalyst Based on a Mixed Oxide of Mo—Te—V—Nb—O by the Hydrothermal Method, Modifying the Calcination Temperature 26.5 g of ammonium heptamolybdate tetrahydrate and 5.75 g of telluric acid are dissolved in 195.0 g of water at 80° C. Ammonium hydroxide (25% aqueous solution) is then added as far as pH=7.5. The water is evaporated from the solution obtained, with stirring, at 80° C. The resulting solid is dried in a kiln at 90° C. with the solid MT being obtained.

Figure 4:
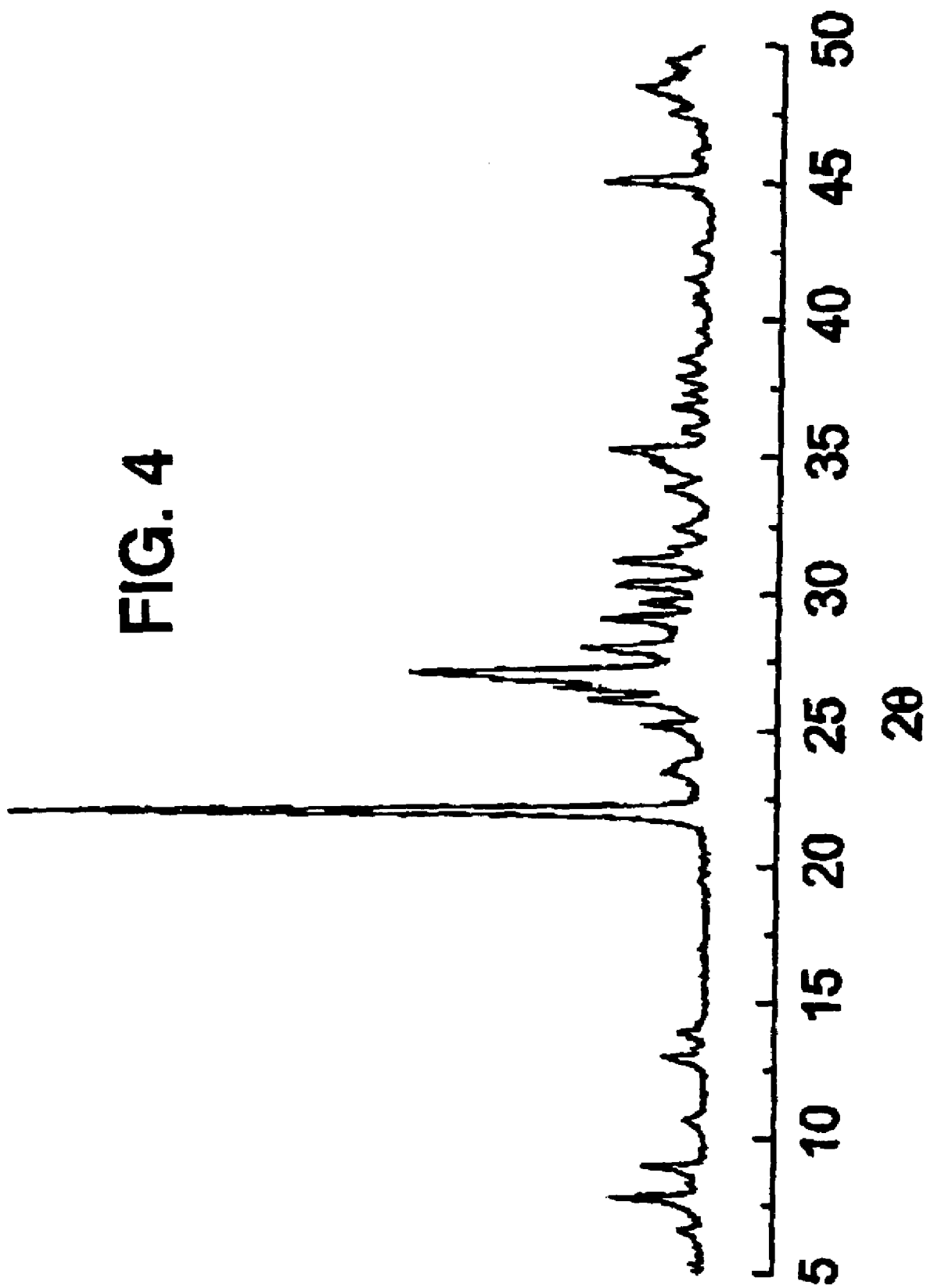
FIG. 4 shows an-X-ray difractogram of the catalyst described in example 7.

30.0 g of the solid MT are suspended in 213.30 g of water at 80° C. and 9.01 g of yanadyl sulphate and 10.39 g of niobium (V) oxalate are added. The mixture is stirred and transferred to a steel autoclave with an internal lining of teflon. The autoclave is kept at 175° C., static, for 2 days The content of the autoclave is filtered, it is washed with distilled water and dried at 80° C. The solid obtained is calcined at 600° C. for 2 h in a current of nitrogen in order to obtain the catalyst. This catalyst is characterized by presenting an X-ray difractogram as shown in FIG. 4. The X-ray diffraction results indicate the formation of various crystalline phases not observed in the catalyst of example 1.

Example 8

Use of the Catalyst Described in Example 5 for the Oxidative Dehydrogenation of Ethane 2.5 g of the solid calcined in example 7 were introduced into a fixed bed quartz reactor. The reaction was carried out using a mixture of gases, with a molar ratio of ethane:oxygen:helium=30/10/60, at a reaction temperature of 400° C. and a contact time, W/F, of 130 $g_{cat}$ h/(mol$_{C2}$). The results are shown in table 2. From the results obtained, it is shown that the calcination temperature modifies the structure of the catalyst and the catalytic properties (conversion of ethane, selectivity to ethene) of these catalysts.

Example 9

Preparation of an Oxidation Catalyst Based on a Mixed Oxide of Mo—Te—V—Nb—Cu Modifying the Synthesis Conditions 26.5 g of ammonium heptamolybdate tetrahydrate and 5.75 g of telluric acid are dissolved in 195.0 g of water at 80° C. Ammonium hydroxide (25% aqueous solution) is then added as far as pH=7.5. The water is evaporated from the solution obtained, with stirring, at 80° C. The resulting solid is dried in a kiln at 90° C. with the solid MT being obtained.

30.0 g of the solid MT are suspended in 213.30 g of water at 80° C. and 9.01 g of yanadyl sulphate and 10.39 g of niobium (V) oxalate are added. The mixture is stirred and transferred to a steel autoclave with an internal lining of teflon. The autoclave is kept at 175° C., static, for 60 h The content of the autoclave is filtered, it is washed with distilled water and dried at 80° C. The solid obtained is calcined at 600° C. for 2 h in a current of nitrogen.

Figure 5:
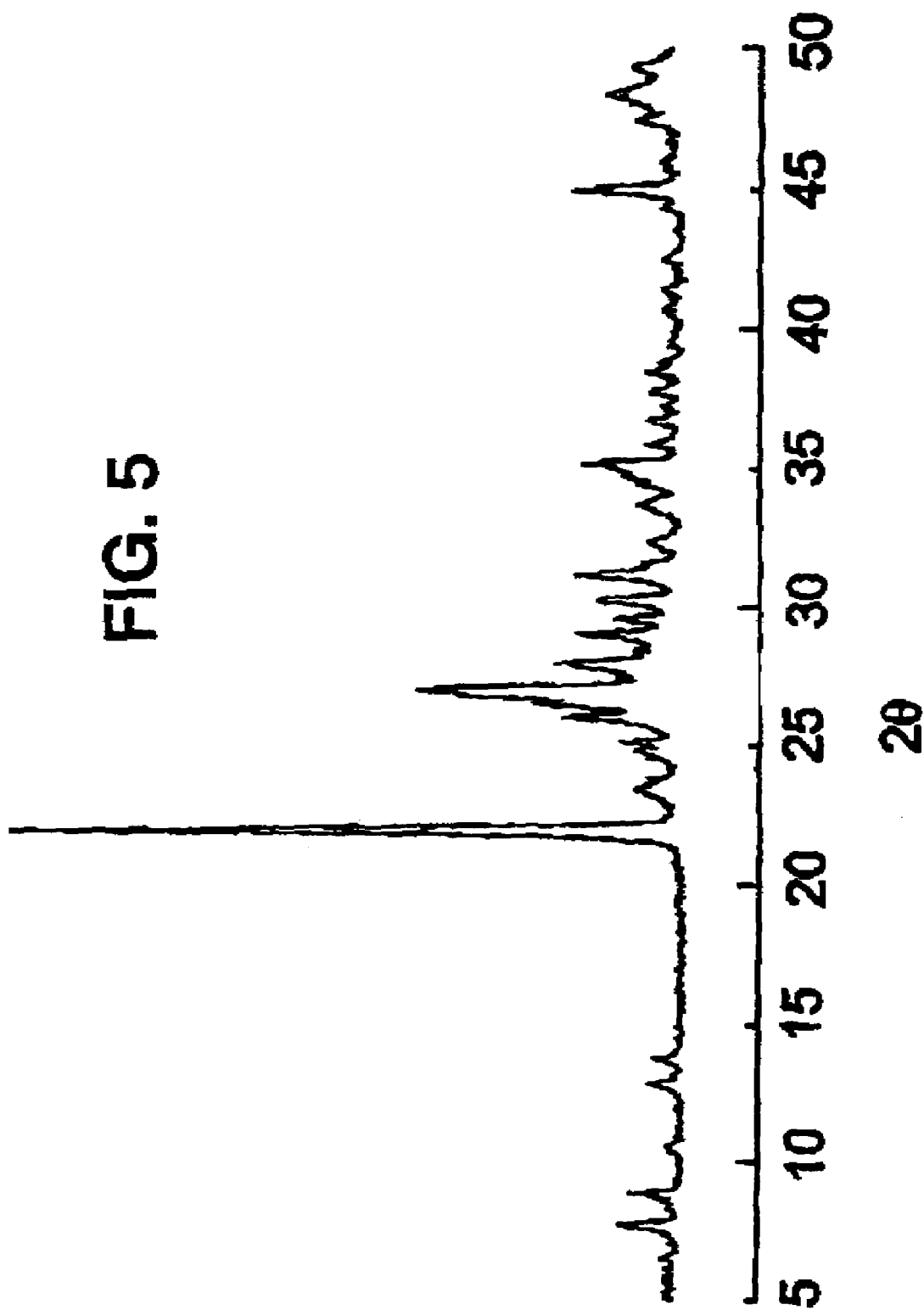
FIG. 5 shows an-X-ray difractogram of the catalyst described in example 9.

10.0 g of the calcined solid are suspended in 10.0 ml of an aqueous solution with 0.080 g of copper (II) nitrate. Once the water has evaporated, the resulting solid was dried in a kiln at 110° C. for 24 h and was ground in order to obtain particle sizes of less than 0.25 mm. The resulting powder was calcined at 600° C. for 1 h in a nitrogen atmosphere in order to obtain the catalyst. The X-ray difractogram of that catalyst is shown in FIG. 5.

Example 10

Use of the Catalyst Described in Example 9 for the Oxidative Dehydrogenation of Ethane 2.5 g of the solid calcined in example 9 were introduced into a fixed bed quartz reactor. The reaction was carried out using a mixture of gases, with a molar ratio of ethane:oxygen:helium=30/10/60, at a reaction temperature of 400° C. and a contact time, W/F, of 74 $g_{cat}$ h/(mol$_{C2}$). The results are shown in table 2.

Example 11

Preparation of an Oxidation Catalyst Similar to that of Example 7 Modifying the Synthesis Conditions 26.5 g of ammonium heptamolybdate tetrahydrate and 5.75 g of telluric acid are dissolved in 195.0 g of water at 80° C. Ammonium hydroxide (25% aqueous solution) is then added as far as pH=7.5. The water is evaporated from the solution obtained, with stirring, at 80° C. The resulting solid is dried in a kiln at 90° C. with the solid MT being obtained.

Figure 6:
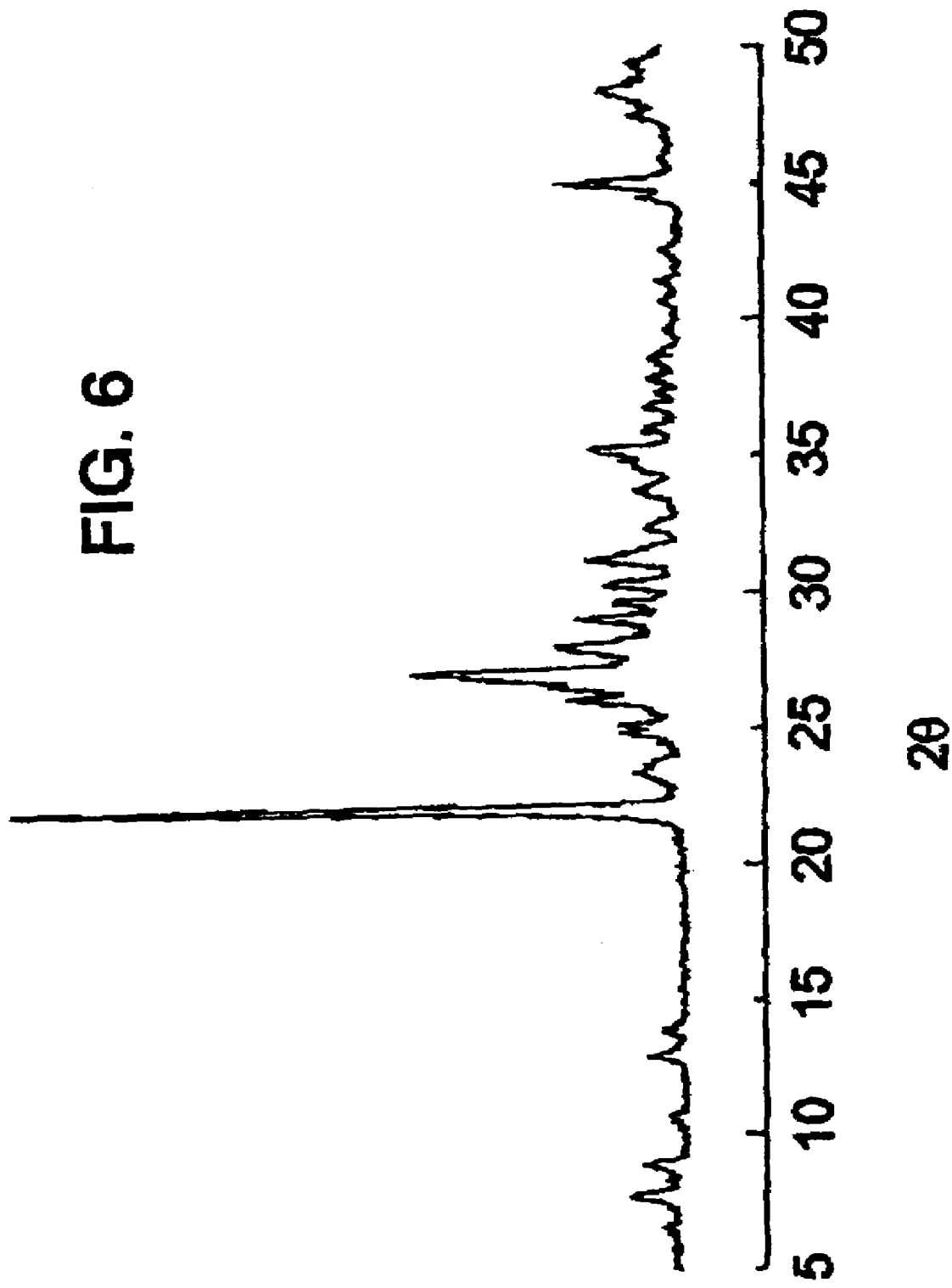
FIG. 6 shows an-X-ray difractogram of the catalyst described in example 11.

30.0 g of the solid MT are suspended in 213.30 g of water at 80° C. and 9.01 g of yanadyl sulphate and 10.39 g of niobium (V) oxalate are added. The mixture is stirred and transferred to a steel autoclave with an internal lining of teflon. The autoclave is kept at 175° C., static, for 60 h. The content of the autoclave is filtered, it is washed with distilled water and dried at 80° C. The solid obtained is calcined for 2 h at 600° C. in a current of nitrogen in order to obtain the catalyst. The X-ray difractogram of that catalyst is shown in FIG. 6.

Example 12

Use of the Catalyst Described in Example 11 for the Oxidative Dehydrogenation of Ethane 2.0 g of the solid calcined in example 11 were introduced into a fixed bed quartz reactor. The reaction was carried out using a mixture of gases, with a molar ratio of ethane:oxygen:helium=30/10/60, at a reaction temperature of 400° C. and a contact time, W/F, of 45 $g_{cat}$ h/(mol$_{C2}$). The results are shown in table 2.

Example 13

Use of the Catalyst Described in Example 11 Modifying the Reaction Conditions 2.0 g of the solid calcined in example 11 were introduced into a fixed bed quartz reactor. The reaction was carried out using a mixture of gases, with a molar ratio of ethane:oxygen:helium=9/6/85, at a reaction temperature of 400° C. and a contact time, W/F, of 270 $g_{cat}$ h/(mol$_{C2}$). The results are shown in table 2.

Example 14

Use of the Catalyst Described in Example 11 Modifying the Reaction Conditions 2.0 g of the solid calcined in example 11 were introduced into a fixed bed quartz reactor. The reaction was carried out using a mixture of gases, with a molar ratio of ethane: oxygen:helium=30/30/40, at a reaction temperature of 400° C. and a contact time, W/F, of 170 $g_{cat}$ h/(mol$_{C2}$). The results are shown in table 2.

Example 15

Preparation of an Oxidation Catalyst Starting from a Solution Containing Mo—V—Te—Nb Modifying the Preparation Method 80.0 g of ammonium heptamolybdate tetrahydrate, 15.87 g of ammonium metavanadate and 23.97 g of telluric acid were dissolved in 1307 ml of hot water at 80° C. obtaining a uniform solution. Also, and after warming to 40° C., a solution (356.8 g) was prepared of niobium oxalate containing 53.97 millimols of niobium and it was added to the above solution obtaining a solution. The water of this solution was eliminated by evaporating with a rotavapor at 50° C., obtaining a solid. This solid was dried in a kiln at 110° C. for 24 h and was ground in order to obtain particle sizes of less than 0.25 mm. The resulting powder was calcined at 600° C. for 2 h in a nitrogen atmosphere in order to obtain the catalyst. The X-ray difractogram of that catalyst is shown in FIG. 7.

Example 16

Use of the Catalyst Described in Example 15 for the Oxidative Dehydrogenation of Ethane 10.0 g of the solid calcined in example 15 were introduced into a fixed bed quartz reactor. The reaction was carried out using a mixture of gases, with a molar ratio of ethane: oxygen:helium=30/10/60, at a reaction temperature of 340° C. and a contact time, W/F, of 134 $g_{cat}$ h/(mol$_{C2}$). The results are shown in table 2.

Example 17

Use of the Catalyst Described in Example 15 for the Oxidative Dehydrogenation of Ethane with Different Reaction Conditions 2.5 g of the solid calcined in example 15 were introduced into a fixed bed quartz reactor. The reaction was carried out using a mixture of gases, with a molar ratio of ethane: oxygen:helium=9/6/85, at a reaction temperature of 400° C. and a contact time, W/F, of 222 $g_{cat}$ h/(mol$_{C2}$). The results are shown in table 2.

Example 18

Preparation of an Oxidation Catalyst Starting from a Solution Containing Mo—V—Te—Nb—Bi Modifying the Preparation Method 80.0 g of ammonium heptamolybdate tetrahydrate, 15.87 g of ammonium metavanadate, 0.280 g of bismuth nitrate and 23.97 g of telluric acid were dissolved in 1307 ml of hot water at 80° C. obtaining a uniform solution. Also, and after warming to 40° C., a solution (356.8 g) was prepared of niobium oxalate containing 53.97 millimols of niobium and it was added to the above solution obtaining a solution. The water of this solution was eliminated by evaporating with a rotavapor at 50° C., obtaining a solid. This solid was dried in a kiln at 110° C. for 24 h and was ground in order to obtain particle sizes of less than 0.25 mm. The resulting powder was calcined at 600° C. for 2 h in a nitrogen atmosphere in order to obtain the catalyst.

Example 19

Use of the Catalyst Described in Example 18 for the Oxidative Dehydrogenation of Ethane with Different Reaction Conditions 2.5 g of the solid calcined in example 18 were introduced into a fixed bed quartz reactor. The reaction was carried out using a mixture of gases, with a molar ratio of ethane: oxygen:helium=9/6/85, at a reaction temperature of 400° C. and a contact time, W/F, of 222 $g_{cat}$ h/(mol$_{C2}$). The results are shown in table 2.

TABLE 2

Catalysis results for the oxidative dehydrogenation of ethane

| Example | Catalyst | Calcination Temperature ° C. | W/F | $C_3H_6/O_2$/He | Reaction temperature ° C. | Ethane conversion (%) | Selectivity to ethene (%) | Yield of ethene (%)[1] |
|---|---|---|---|---|---|---|---|---|
| 2 | MoVTeNb | 425 | 160 | 30/10/60 | 400 | 49.1 | 69.6 | 28.8 |
| 4 | MoVNb | 425 | 20, 4 | 30/10/60 | 400 | 21.5 | 60.5 | 13.0 |
| 6 | MoVTe | 425 | 240 | 30/10/60 | 400 | 1.9 | 51.4 | 0.98 |
| 8 | MoVTeNb | 600 | 130 | 30/10/60 | 400 | 42.5 | 87.8 | 37.3 |
| 10 | MoVTeNbCu | 600 | 74 | 30/10/60 | 400 | 40.3 | 91.0 | 36.7 |
| 12 | MoVTeNb-B | 600 | 45 | 30/10/60 | 400 | 41.4 | 92.5 | 38.3 |
| 13 | MoVTeNb-B | 600 | 270 | 9/6/85 | 400 | 63.3 | 88.7 | 56.1 |
| 14 | MoVTeNb-B | 600 | 173 | 30/10/60 | 400 | 80.9 | 79.2 | 64.1 |
| 16 | MoVTeNb-C | 600 | 134 | 30/10/60 | 340 | 24.4 | 95.5 | 23.3 |
| 17 | MoVTeNb-C | 600 | 222 | 9/6/85 | 400 | 57.2 | 90.3 | 51.7 |
| 19 | MoVTeNbBi | 600 | 222 | 9/6/85 | 400 | 60.2 | 90.3 | 54.4 |

The invention claimed is:

1. A method for the oxidative dehydrogenation of ethane, comprising placing ethane in contact with a catalyst comprising Mo, Te, V, Nb and at least a fifth element A which is selected from the group consisting of Cu, Ta, Sn, Se, W, Ti, Fe, Co, Ni, Cr, Zr, Sb, Bi, an alkali metal, an alkaline-earth metal and a rare earth, and which, in calcined form, presents an X-ray diffractogram with intense diffraction lines corresponding to diffraction angles 2Θ of 7.7°±0.4, 8.90°±0.4, 22.1°±0.4, 26.6°±0.4, 26.9°±0.4, 27.1°±0.4, 28.1°±0.4, 31.2°±0.4, 35.0°±0.4, and 45.06°±0.4.

2. A method in accordance with claim 1, wherein the catalyst has the empirical formula:

$$MoTe_h V_i Nb_j A_k O_x$$

in which
h, is comprised between 0.1 and 1.0,
i is comprised between 0.02 and 1.0,
j is comprised between 0.00 1 and 1.0
k is comprised between 0.0001 and 1.0 and
x has a value which depends on the oxidation state of the elements Mo, Te, V, Nb and A.

3. A method in accordance with claim 2, wherein the catalyst has the empirical formula:

$$MoTe_h V_i Nb_j A_k O_x$$

wherein
h and i are comprised between 0.1 and 0.8,
the ratio i/h is comprised between 0.1 and 8,
j is comprised between 0.001 and 1, and
k is comprised between 0.0001 and 1.0.

4. A method in accordance with claim 1, 2 or 3, wherein the catalyst comprises an element A selected from the group consisting of Cu, W, Bi and mixtures thereof.

5. A method in accordance with claim 2 or 3, wherein the catalyst comprises an element A selected from the group consisting of Cu, W and Bi and
h and i are comprised between 0.1 and 1,
the ratio i/h is comprised between 0.1 and 10,
j is comprised between 0.01 and 0.8, and
k is comprised between 0.0002 and 0.05.

6. A method in accordance with claim 1, wherein the catalyst presents an X-ray diffractogram comprising the following diffraction lines

| Diffraction angle 2Θ (±0.4)° | Mean spacing (Å) | Relative intensity |
|---|---|---|
| 7.7 | 11.47 | 10-40 |
| 8.9 | 9.93 | 10-40 |
| 22.1 | 4.02 | 100 |
| 26.1 | 3.35 | 10-90 |
| 26.9 | 3.31 | 20-80 |
| 27.1 | 3.29 | 20-120 |
| 28.1 | 3.17 | 20-120 |
| 31.2 | 2.86 | 10-90 |
| 35.2 | 2.56 | 10-90 |
| 45.1 | 2.01 | 10-60. |

7. A method in accordance with claim 1, wherein in the catalyst at least Mo, Te, V and Nb are present in the form of at least one calcined mixed oxide.

8. A method in accordance with claim 1, wherein the catalyst is a calcined mixed oxide.

9. A method in accordance with claim 1, wherein the catalyst is a mixed oxide supported on a solid.

10. A method in accordance with claim 9, wherein the solid is selected from the group consisting of silica, alumina, titanium oxide and mixtures thereof.

11. A method in accordance with claim 9, wherein the solid is silica contained in a proportion of 20 to 70% by weight of the total weight of catalyst.

12. A method in accordance with claim 9, wherein the solid is silicon carbide.

13. A method in accordance with claim 1, wherein said oxidative dehydrogenation of ethane produces ethene.

14. A method in accordance with claim 13, wherein said oxidative dehydrogenation of ethane to ethene is carried out in a gaseous phase and in the presence of water vapour.

15. A method in accordance with claim 1 wherein said oxidative dehydrogenation of ethane gives rise to acetic acid.

16. A method in accordance with claim 15, wherein said oxidative dehydrogenation of ethane to acetic acid is carried out by reaction of ethane and oxygen in gaseous phase in the presence of water.

17. A method in accordance with claim 1, wherein said oxidative dehydrogenation of ethane gives rise to acetonitrile.

18. A method in accordance with claim 17, wherein oxidative dehydrogenation of ethane to acetonitrile is carried out by reaction of ethane and oxygen, in the gaseous phase in the presence of ammonia and water vapour.

19. A method in accordance with claim 1, wherein said oxidative dehydrogenation is carried out using the catalyst as a co-catalyst.

20. A method in accordance with claim 19, wherein said oxidative dehydrogenation of ethane is carried out using the catalyst as a co-catalyst, so that the oxidation of ethane to ethene takes place.

21. A method in accordance with claim 19, wherein said oxidative dehydrogenation of ethane is carried out using the catalyst as co-catalyst, so that the oxidation of ethane to acetic acid takes place.

22. A method in accordance with claim 19, wherein said oxidative dehydrogenation of ethane is carried out using the catalyst as co-catalyst, so that ammoxidation of ethane to acetonitrile takes place.

23. A method in accordance with claim 19, wherein said oxidative dehydrogenation of ethane is carried out using the catalyst as co-catalyst, so that oxidation of ethane to ethylene oxide takes place.

24. A method in accordance with claim 1, wherein the catalyst comprises an element A selected from the group consisting of Cu, W and Bi and presents an X-ray diffractogram comprising the following diffraction lines

| Diffraction angle 2Θ (±0.4)° | Mean spacing (Å) | Relative Intensity |
|---|---|---|
| 7.7 | 11.47 | 10-40 |
| 8.9 | 9.93 | 10-40 |
| 22.1 | 4.02 | 100 |
| 26.1 | 3.35 | 10-90 |
| 26.9 | 3.31 | 20-80 |
| 27.1 | 3.29 | 20-120 |
| 28.1 | 3.17 | 20-120 |
| 31.2 | 2.86 | 10-90 |
| 35.2 | 2.56 | 10-90 |
| 45.1 | 2.01 | 10-60. |

* * * * *